United States Patent [19]

Rohrbach et al.

[11] 4,250,260

[45] Feb. 10, 1981

[54] REGENERATION OF AN IMMOBILIZED ENZYME SYSTEM

[75] Inventors: Ronald P. Rohrbach, Forest Lake, Ill.; Joseph Levy, Deerfield Beach, Fla.

[73] Assignee: UOP Inc., Des Plaines, Ill.

[21] Appl. No.: 68,803

[22] Filed: Aug. 22, 1979

[51] Int. Cl.³ .............. C12M 11/14; C12M 11/08; C12M 11/06; B01J 31/40
[52] U.S. Cl. ......................... 435/176; 252/413; 435/180; 435/181
[58] Field of Search .............. 252/413, 414, 430, 428; 435/180, 181, 182, 174–177

[56] References Cited

U.S. PATENT DOCUMENTS

| | | | |
|---|---|---|---|
| 3,761,357 | 9/1973 | Epton et al. | 435/181 |
| 3,836,433 | 9/1974 | Wirth et al. | 435/181 |
| 4,113,568 | 9/1978 | Fujita et al. | 435/180 |
| 4,141,857 | 2/1979 | Levy et al. | 252/430 |

*Primary Examiner*—P. E. Konopka
*Attorney, Agent, or Firm*—James R. Hoatson, Jr.; Raymond H. Nelson; William H. Page, II

[57] ABSTRACT

A method for regenerating an immobilized enzyme system comprises treating the system with an acid, removing excess acid, treating the system with a bifunctional organic reagent which furnishes a pendant group, removing excess of said bifunctional reagent, and immobilizing fresh, active enzyme.

7 Claims, 1 Drawing Figure

Immobilized Enzyme System

Immobilized Enzyme System
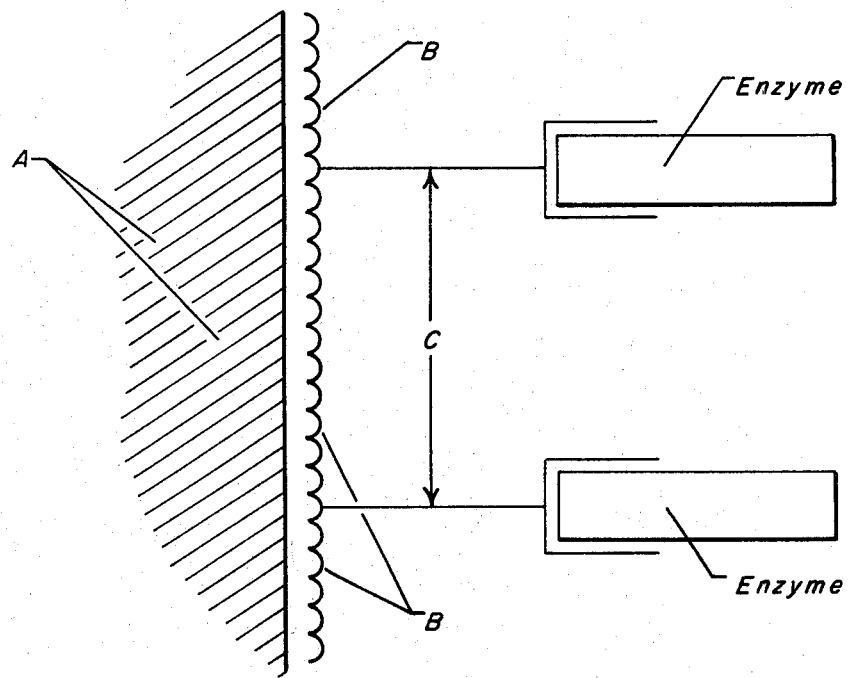

REGENERATION OF AN IMMOBILIZED ENZYME SYSTEM

BACKGROUND OF THE INVENTION

Enzyme-catalyzed reactions often have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzyme for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in Levy and Fusee, U.S. Pat. No. 4,141,857, where a polyamine is adsorbed on a metal oxide such as alumina, treated with an excess of a bifunctional reagent, such as glutaraldehyde, so as to cross-link the amine, thereby entrapping the resulting polymer in the pores of the metal oxide, and then contacting the mass with enzyme to form covalent bonds between the pendant aldehyde groups and an amino group on the enzyme.

The useful life of an immobilized enzyme system is limited by a continual decrease in enzymatic activity. Among the many mechanisms which lead to enzyme deactivation in such systems are: poisoning of the enzymes by impurities in the feedstock; other chemical modification of the enzyme during its utilization; denaturation of the enzyme; rupture of the bond between the pendant group and the enzyme leading to dissolution of the enzyme; cleavage of the bond between the pendant group and the intermediate binding layer; loss of the binding layer as, for example, by physical ablation or cleavage of the chemical bonds which hold it to the support.

Whatever the mechanism of the enzyme deactivation, reactivation of a deactivated immobilized enzyme system would prove to be a substantial advance in the art as well as being economically highly desirable. At least conceptually, two distinct approaches to reactivation are possible. One mode would be to rejuvenate the enzyme itself, i.e., assuming no physical loss of enzyme, the transformations which rendered it inactive would be reversed and the enzyme would revert to its initial active state. The alternative is to restore the immobilized enzyme system to that state initially present immediately prior to attachment of enzyme, so that it would be capable of binding fresh, active enzyme once again. This invention relates to the latter approach.

SUMMARY OF THE INVENTION

An object of this invention is to regenerate an immobilized enzyme system which has become substantially deactivated. An embodiment of this invention resides in a process for regenerating an immobilized enzyme system comprising treating the system with an acid as an enzyme stripping agent, removing the acid, treating the system with a bifunctional organic molecule which provides a pendant group, and removing the excess of bifunctional organic molecule, so as to put the system in a state where fresh, active enzyme can be immobilized by suitable means. A more specific embodiment of this invention resides in the application of this process to a system wherein the binding layer is an organic polymer material and the pendant functional moiety can bond covalently with an enzyme without destroying its activity. Another more specific embodiment of this invention is the application of this process wherein the enzyme is glucose isomerase and the stripping agent is hydrochloric acid. Other objects and embodiments will be apparent from the description provided herein.

It is to be emphasized that enzymes are merely representative of one class of reactive chemical entities which may be immobilized to act in some chemical process. Therefore, this invention encompasses regeneration of any immobilized reactive chemical entity which has become substantially deactivated.

DESCRIPTION OF THE FIGURE

Many immobilized enzyme systems, such as that described above, have a common conceptual basis which is depicted pictorially in the FIGURE. It is to be understood that enzymes are merely one class of reactive chemical entities which may be immobilized and subsequently utilized in a chemical process.

There is a central core support, A, whose primary purpose is to provide mechanical and thermal stability to the system and which is chemically inert in the enzymatic reaction. The intermediate bonding layer, B, provides an interface between the core and the pendant groups, C. This layer may be held to the core either by physical entrapment, as within the pores of A, by strong short-range physical and/or chemical forces, as by surface adsorption or absorption, or by chemical binding to the surface of the core support. The pendant groups, C, may be part of the molecular structure of the binding layer, or may be chemically bonded to a suitable site on the binding layer. Such pendant groups are characterized by the presence of a chemically reactive functionality, usually terminally situated, which can covalently bond to some part of the enzyme, or other reactive chemical entity, sufficiently removed from its "active site" so as not to interfere substantially with its catalytic activity.

DESCRIPTION OF THE INVENTION

Although several kinds of immobilized enzyme systems are available, those wherein the enzyme is covalently bonded to a support seem to offer the best compromise between enzyme availability to feedstock and long-term immobility on a supporting structure. Accordingly, emphasis is placed on stripping deactivated enzyme and regenerating such an active immobilized enzyme system. This invention relates to the structure depicted in the FIGURE. The central core support, A in the FIGURE, may be a metal oxide, preferably alumina and silica, glass, a ceramic or a metal. It needs to provide structural integrity, especially mechanical strength, have good characteristics in a system where there is a liquid flow, and provide a surface, wholly or in part, to which a layer of organic material can be attached either by physical or chemical means, or by a combination of the latter.

The binding layer, B, may be an organic polymer or a resin. Examples of such binding layers include functionalized polyethylenes, polyamines cross-linked with agents such as dialdehydes and diisocyanates, and others known to those skilled in the art. In a preferred embodiment the binding layer is a polyamine, such as polyethyleneimine, tetraethylenepentamine, ethylenediamine, diethylenetriamine, triethylenetetramine, pentaethylenehexamine, hexamethylenediamine, phenylenediamine, and the like, cross-linked via a reagent selected from the group consisting of dialdehydes and diisocyanates, as for example glutaraldehyde, succindialdehyde, toluenediisocyanate, and the like. In another preferred embodiment the binding layer is a functionalized polystyrene, such as aminopolystyrene, cross-linked by one of the aforementioned agents.

The pendant group, C, may be an independently functionalized group of the polymer, as for example an aldehydic moiety attached via mediating carbon atoms to a polyethylene chain, an independently functionalized group of a resin, or an unreacted terminus of the cross-linking agent wherein the other terminus is covalently bonded to the binding layer. In a preferred embodiment the pendant group arises from a cross-linking agent selected from the group consisting of dialdehydes and diisocyanates.

In some instances the demarcation between core support, A, binding layer, B, and pendant group, C, may seem indistinct. For example, the binding layer may appear to be part of the core, and might even contain a functional group which can covalently bond to an enzyme, thereby providing an immobilized enzyme system. A representative of this class is a chemically modified glass whose surface bears an organic residue having a functional group capable of covalently bonding to an enzyme. This invention relates to such a system, and to all systems which are functionally equivalent to, or can be functionally described by the representation in the FIGURE, however that may be attained in any specific immobilized enzyme system. The combination of the structures A, B, and C forms a support system; addition of enzyme forms an immobilized enzyme system.

The method of stripping and regeneration taught herein may be applied to any immobilized reactive chemical entity in which the reactive molecule can react with the pendant functional group without substantial loss of chemical activity; enzymes form an important class of such reactive molecules. Examples of such enzymes include glucose isomerase, glucoamylase, lactase, cellulase, glucose oxidase, trypsin, papain, hexokinase, chymotrypsin, acylase, invertase, protease, pepsin, rennin, xylanase, beta amylase, gamma amylase, etc. It is to be understood that these enzymes are cited solely for illustrative purposes and it is not be construed as a limitation of this invention. Other enzymes may be utilized, but not necessarily with equivalent results.

The physical form of the immobilized enzyme system generally is determined by factors extraneous to the stripping-regeneration process. Thus the system may be in the form of pellets of, for example, 1/16 inch size, or it may be in the form of smaller spheres of, for example 60–80 mesh. Although the form in which the immobilized enzyme is used may necessitate different optimum parameters in the stripping-regeneration process, the basic method remains unchanged.

Immobilized enzyme systems in which the enzyme has become totally inactive, or nearly so, may be unpacked from the columns where they had been used and placed in containers. To this may be added sufficient enzyme stripping reagent such that the pellets or spheres are completely covered with liquid. Among the stripping reagents which are suitable for use are the strong acids. Examples of such reagents include mineral acids such as hydrochloric, hydrobromic, phosphoric, and sulfuric, and other strong acids as trifluoroacetic acid, trichloroacetic acid, alkylsulfonic acids such as methanesulfonic acid, ethanesulfonic acid, propanesulfonic acid and the like, arylsulfonic acids such as benzenesulfonic acid, p-toluenesulfonic acid, etc. The concentration of the reagent and amount used is not critical, provided that there is sufficient reagent to remove all inactive enzyme at a concentration which will not substantially degrade the support system, and that the volume is sufficient to provide adequate contact with the pellets or spheres. Concentrations of acid employed may range from about 0.01 to about 5 molar. The temperature at which stripping is conducted may be from about 20° C. to about 75° C., preferably from about 50° C. to about 70° C. Contact time may be from about 1 to about 30 minutes, preferably from about 1 to about 10 minutes, and may be accompanied by agitation. In one embodiment the reagent is hydrochloric acid.

After the material has been treated with the acid for an appropriate time, the excess reagent may be removed by decantation. The pellets or spheres are then washed thoroughly with water to remove any acid adhering to the surface. When no more acid is present, the system is ready for contacting with a solution which furnishes the pendant group. For example, the solution may be one of glutaraldehyde in water, where the concentration of glutaraldehyde is not material so long as there is present sufficient material to replace any pendant groups lost. Where the pendant group is reactive toward water, the enzyme support system may have to be dried, by means which will be obvious to those skilled in the art, prior to treatment with the reagent. Although the system generally will be treated with a solution which furnishes the pendant group originally present, it may be treated with a solution which furnishes a different pendant group. Representatives of materials furnishing a pendant group, enumerated solely for the purpose of illustration, include glutaraldehyde, succindialdehyde, terephthalaldehyde, and toluene diisocyanate.

When the enzyme support system has been contacted with a solution furnishing the pendant groups for a time sufficient to replace all those previously lost, which time may vary from about 30 minutes to about 5 hours, depending on the nature of the support system, its history, the stripping reagent used and the nature of the pendant group, it is washed thoroughly to remove unreacted but adhering molecules which furnish the pendant group. At this stage the support system is rejuvenated, which is to say that it approximates its condition prior to initial enzyme immobilization. The support system is now ready to accept fresh, active enzyme to regenerate an immobilized enzyme system whose activity substantially approximates that obtained with a new support. In the case, for example, of a polyethyleneimine binding layer cross-linked with excess glutaraldehyde, glucose isomerase may be immobilized by contacting the support system, with agitation, with an aqueous solution of the enzyme for 6 to 24 hours at a temperature from about 0° to about 50° C. preferably from about 0° to about 10° C. However, it is not an object of this invention to teach how enzymes are best immobilized given a particular support, thus it suffices to say that the support regenerated by the method of this invention is treated with enzyme in whatever way is appropriate for immobilization of that particular enzyme on a particular support system.

The description above is for a stripping-regeneration process run in a batchwise method. However, the process of this invention may be done in a continuous manner where such a mode is advantageous. Thus, as an example where the stripping agent is phosphoric acid and the reagent furnishing the pendant group is glutaraldehyde, the deactivated enzyme system in a column may be treated with a phosphoric acid solution recirculated through the bed for a time sufficient to remove all enzyme. Thereafter the bed may be washed with water until all traces of acidic material are removed, followed by treatment with recirculated glutaraldehyde solution until there is not further uptake of the latter reagent. Unreacted but adhering glutaraldehyde may be removed by treatment with fresh water, after which active enzyme may be immobilized by suitable means.

Whether the stripping portion of the process of this invention consists of selective removal of spent enzyme from the pendant group, or whether it consists of removal of the pendant group from the binding layer, or some combination thereof is not known. This invention is meant to encompass removal of spent enzyme from an enzyme support system of the type described herein whatever the mechanism of removal, and subsequent regeneration to produce an active immobilized enzyme system.

The following examples serve merely to illustrate the process of this invention, and it is to be understood that this invention is not limited thereto.

EXAMPLE 1

An immobilized enzyme system, in the form of 1/16 inch pellets, consisted of aminopolystyrene on alumina cross-linked with glutaraldehyde and bearing glucoamylase. It had been used with a feedstock of 30% starch and 0.2 M acetate buffer at pH 4.2. The bed, whose initial activity was 8.06 units per gram, was removed from the column and treated with 2 molar hydrochloric acid, in an amount sufficient to cover the material, at 60° C. with stirring for 10 minutes. Acid was decanted and solid was washed repeatedly until the washings were neutral. At this stage the material showed no enzymatic activity. A 2.5% solution of glutaraldehyde was added in an amount equal to 18 ml. per gram of bed for about one hour with occasional mixing. Excess glutaraldehyde was removed by decantation followed by thorough washing with water to remove adhering glutaraldehyde. Glucoamylase was immobilized by suitable means to give an immobilized enzyme system whose activity was 8.87 units per gram. Thus the regenerated system has 110% of the activity present initially.

EXAMPLE 2

The immobilized enzyme system was 60–80 mesh alumina coated with polyethyleneimine cross-linked with excess glutaraldehyde and bearing glucose isomerase. When first used in a fixed bed reactor whose feedstock was 45% glucose the system had an activity of 1110 units per gram. The used column was unpacked and the bed material was treated with 20 ml. of 2 molar hydrochloric acid at 60° C. for 30 minutes with stirring. Liquid was removed by decantation and the solid was stirred with sufficient water to cover the solid, after which the water was removed by decantation. This procedure was repeated until the wash water was neutral. An assay of the bed material showed zero glucose isomerase activity. Regeneration of the support system was achieved by contacting the bed with a 2.5% aqueous solution of glutaraldehyde in an amount equivalent to 18 ml. per gram bed material for one hour. Liquid was removed by decantation and excess glutaraldehyde was removed by thorough washing with water. An aqueous solution of glucose isomerase was contacted with the regenerated material for 18 hours at 4° C. with continual shaking. The immobilized enzyme system again was thoroughly washed with water to remove adhering but mobile enzyme. The regenerated immobilized enzyme system had an activity of 760 units per gram or 68% of its original activity.

We claim as our invention:

1. A method for regenerating a used organic-inorganic support matrix comprising an organic polymeric material having functionalized pendant groups coupled with immobilized enzymes which method comprises:
    (a) treating said used support matrix with a stripping agent consisting essentially of a strong acid at stripping conditions which include a temperature of from about 20° to about 75° C.;
    (b) washing said treated support matrix containing immobilized enzymes and said strong acid to remove said strong acid from said treated support matrix;
    (c) treating said washed support matrix of step (b) with a bifunctional organic molecule consisting essentially of a compound selected from the group consisting of glutaraldehyde, succindialdehyde, terephthaladehyde and toluenediiscocyanate to attach pendant organic molecules to said washed support matrix wherein said pendant organic molecules attached to said support matrix are sufficient to replace former pendant organic molecules removed through said use of said support matrix;
    (d) washing said support matrix containing newly attached pendant organic molecules to remove excess organic molecules from said treatment of step (c); and
    (e) immobilizing fresh active enzymes by coupling said enzymes to said newly attached pendant organic molecules.

2. The method of claim 1 wherein the support system is comprised of a central core to which is attached a binding layer, a pendant functional group anchored at the nonfunctional end to said binding layer and wherein said functional group is capable of covalently bonding to enzymes.

3. The method of claim 2 wherein said central core is selected from the group consisting of aluminum oxide, silicon oxide, glass and a ceramic material.

4. The method of claim 2 wherein said binding layer is selected from the group consisting of cross-linked polyamines and cross-linked aminopolystyrenes.

5. The method of claim 4 wherein said binding layer is a polyamine selected from the group consisting of polyethyleneimine, tetraethylenepentamine, ethylenediamine, diethylenetriamine, triethylenetetramine, pentaethylenehexamine, hexamethylenediamine, and phenylenediamine, and the cross-linking agent is selected from the group consisting of glutaraldehyde, succindialdehyde, and toluenediisocyanate.

6. The method of claim 1 wherein said strong acid stripping agent is selected from the group consisting of hydrochloric acid, phosphoric acid, hydrobromic acid, sulfuric acid, trifluoroacetic acid, trichloroacetic acid, methanesulfonic acid, benzenesulfonic acid, and p-toluenesulfonic acid.

7. The process of claim 1 wherein the enzyme immobilized is selected from the group consisting of glucose isomerase, glucoamylase, and cellulase.

* * * * *